US012560610B2

(12) United States Patent
Kehlet et al.

(10) Patent No.: US 12,560,610 B2
(45) Date of Patent: Feb. 24, 2026

(54) SPARC ASSAY

(71) Applicant: Nordic Bioscience A/S, Herlev (DK)

(72) Inventors: Stephanie Nina Kehlet, Frederiksberg (DK); Diana Øersnes-Leeming, Klampenborg (DK); Morten Karsdal, Kobenhavn Ø (DK)

(73) Assignee: Nordic Bioscience A/S, Herlev (DK)

( * ) Notice: Subject to any disclaimer, the term of this patent is extended or adjusted under 35 U.S.C. 154(b) by 772 days.

(21) Appl. No.: 17/930,548

(22) Filed: Sep. 8, 2022

(65) Prior Publication Data

US 2023/0152323 A1     May 18, 2023

Related U.S. Application Data

(63) Continuation-in-part of application No. 16/956,318, filed as application No. PCT/EP2018/084841 on Dec. 13, 2018, now abandoned.

(30) Foreign Application Priority Data

Dec. 19, 2017   (GB) ...................................... 1721308

(51) Int. Cl.
| | |
|---|---|
| *G01N 33/53* | (2006.01) |
| *C07K 16/00* | (2006.01) |
| *C07K 16/18* | (2006.01) |
| *C07K 16/46* | (2006.01) |
| *G01N 33/534* | (2006.01) |
| *G01N 33/574* | (2006.01) |
| *G01N 33/577* | (2006.01) |
| *G01N 33/00* | (2006.01) |

(52) U.S. Cl.
CPC ....... *G01N 33/57423* (2013.01); *C07K 16/18* (2013.01); *G01N 33/534* (2013.01); *G01N 33/57484* (2013.01); *G01N 33/577* (2013.01); *G01N 33/0093* (2024.05); *G01N 2800/52* (2013.01)

(58) Field of Classification Search
None
See application file for complete search history.

(56) References Cited

PUBLICATIONS

Kehlet et al. Effect of MMP-13 degraded SPARC on type I collagen and its biomarker potential in colorectal cancer. Journal of Clinical Oncology, 2018, 36:4, suppl, 717-717. (Year: 2018).*
Salaun et al. MMP-13 In-Vivo Molecular Imaging Reveals Early Expression in Lung Adenocarcinoma. PLoS One 10(7): e0132960. (Year: 2015).*
Sasaki et al. Immunochemical and tissue analysis of protease generated neoepitopes of BM-40 (osteonectin, SPARC) which are correlated to a higher affinity binding to collagens. Matrix Biology 18:499-508, 1999. (Year: 1999).*
Mort et al. The use of cleavage site specific antibodies to delineate protein processing and breakdown pathway. Mol Patho. 1999; 52(1):11-8. (Year: 1999).*
Koukourakis et al. Enhanced Expression of SPARC/Osteonectin in the Tumor-associated Stroma of Non-Small Cell Lung Cancer Is Correlated with Markers of Hypoxia/ Acidity and with Poor Prognosis of Patients. Cancer Research 63, 5376-5380, Sep. 1, 2003. (Year: 2003).*
Sangaletti et al. SPARC Oppositely Regulates Inflammation and Fibrosis in Bleomycin-Induced Lung Damage. Am J Pathol. Dec. 2011; 179(6): 3000-3010. (Year: 2011).*

* cited by examiner

*Primary Examiner* — Maher M Haddad
(74) *Attorney, Agent, or Firm* — Benjamin Aaron Adler

(57) ABSTRACT

The present invention relates to an assay for detecting secreted proteome acidic and rich in cysteine (SPARC), and more specifically to its use in evaluating lung cancer.

11 Claims, 4 Drawing Sheets

Specification includes a Sequence Listing.

SPARC ASSAY

CROSS-REFERENCE TO RELATED APPLICATIONS

This is a continuation-in-part application under 35 U.S.C. § 120 of pending application U.S. Ser. No. 16/956,318, filed Jun. 19, 2020, which is a national stage application under 35 U.S.C. § 371 of International Application PCT/EP2018/084841, filed Dec. 13, 2018, now abandoned, which claimed priority to European Application No. 1721308.3, filed Dec. 19, 2017, now abandoned.

REFERENCE TO AN ELECTRONIC SEQUENCE LISTING

The contents of the electronic sequence D7756CIPSEQ.xml with a size of 23 kb and created on Aug. 2, 2022 is hereby incorporated by reference in its entirety.

BACKGROUND OF THE INVENTION

Field of the Invention

The present invention relates to an assay for detecting secreted proteome acidic and rich in cysteine (SPARC), and more specifically to its use in evaluating lung cancer.

Description of the Related Art

Secreted proteome acidic and rich in cysteine (SPARC), also referred to as osteonectin or basement membrane protein 40 (BM-40), is a 32-kDa matricellular protein regulating extracellular matrix (ECM) assembly and deposition, growth factor signaling and interactions between cells and their surrounding ECM (1,2). The expression of SPARC is elevated during embryonic development and is decreased in normal adult tissues. However, its expression is increased in epithelial/endothelial cells with a high ECM turnover, during abnormal tissue growth associated with neoplasia and during tissue injury and inflammation, highlighting the importance of SPARC in tissue remodeling (3-5).

SPARC has been shown to have chaperone like activity by inhibiting thermal aggregation of alcohol dehydrogenase in a concentration-dependent manner (6). Furthermore, several studies have shown that SPARC binds different collagens in the ECM and is important for correct collagen deposition and assembly (7-13). The chaperone activity of SPARC is regulated by different factors. A moderate extracellular concentration of $Ca^{2+}$ has been shown to be necessary for binding of SPARC to its ECM partners. The presence of extracellular proteases is another important switch in the regulation of its collagen binding activity. Studies have shown that different metalloproteinases (MMP's) can cleave SPARC at a specific site which increases the affinity for collagens up to 20-fold (14, 15). Interestingly, SPARC has been shown to increase the expression of MMP's in fibroblasts (16-18) causing a positive feedback loop. If this feedback mechanism becomes uncontrolled, it might be involved in the pathology of fibrotic disorders with increased collagen deposition.

Fibrosis is a part of the pathology and/or an end-point in many diseases such as cancer, hypertension, liver cirrhosis and fibrotic lung disorders. Fibrosis is characterized by an increased deposition of ECM, including collagens, which interferes with normal tissue function leading to organ failure. SPARC is known to be an important factor for fibrogenesis (19-23). Wild-type mice with bleomycin induced pulmonary fibrosis have been shown to have an increased amount of collagens within the lungs compared to SPARC-null mice suggesting a higher fibrotic response occurring when SPARC is present (19, 20). Furthermore, SPARC expression has been shown to be upregulated in fibrosis and cancer (24-27).

SUMMARY OF THE INVENTION

The present inventors have now developed a highly sensitive SPARC assay that correlates, to a high degree, with patients suffering from lung cancer. The assay can distinguish between lung cancer and other fibrotic diseases and thus shows excellent diagnostic utility in the evaluation of lung cancer. The assay has also been found to have promising utility in the evaluation of idiopathic pulmonary fibrosis (IPF).

Accordingly, in a first aspect the present invention relates to a method of immunoassay for detecting and/or monitoring the progression of lung cancer in a patient, the method comprising contacting a patient biofluid sample with a monoclonal antibody specifically reactive with an N-terminus amino acid sequence (SEQ ID NO: 1)
    LLARDFEKNY, wherein the monoclonal antibody does not specifically recognise or bind an N-extended elongated version of said N-terminus amino acid sequence or an N-truncated shortened version of said N-terminus amino acid sequence, determining the amount of binding between said monoclonal antibody and peptides comprising said N-terminus amino acid sequence, and correlating said amount of binding with values associated with normal healthy subjects and/or values associated with known lung cancer severity and/or values obtained from said patient at a previous time point and/or a predetermined cut-off value.

As noted above, the monoclonal antibody does not specifically recognise or bind an N-extended elongated version of said N-terminus amino acid sequence or an N-truncated shortened version of said N-terminus amino acid sequence. In this regard "N-extended elongated version of said N-terminus amino acid sequence" means one or more amino acids extending beyond the N-terminus of the sequence (SEQ ID NO: 1)
    $H_2N$-LLARDFEKNY.

For example, if the N-terminal amino acid sequence (SEQ ID NO: 1)
    $H_2N$-LLARDFEKNY was elongated by a glutamic acid residue then the corresponding "N-extended elongated version" would be (SEQ ID NO: 2)
    $H_2N$-ELLARDFEKNY.

Similarly, "N-truncated shortened version of said N-terminus amino acid sequence" means one or more amino acids removed from the N-terminus of the sequence (SEQ ID NO: 1)

H₂N-LLARDFEKNY.

For example, if the N-terminal amino acid sequence (SEQ ID NO: 1)

H₂N-LLARDFEKNY was shortened by one amino acid residue then the corresponding "N-truncated shortened version" would be (SEQ ID NO: 3)

H₂N-LARDFEKNY.

Monoclonal antibodies that specifically bind to the N-terminus amino acid sequence (SEQ ID No. 1)

LLARDFEKNY can be generated via an suitable techniques known in the art. For example, the monoclonal antibody may be raised against a synthetic peptide having the amino acid sequence (SEQ ID No. 1)

LLARDFEKNY, such as for example by: immunizing a rodent (or other suitable mammal) with a synthetic peptide consisting of the sequence (SEQ ID No. 1)

LLARDFEKNY, which optionally may linked to an immunogenic carrier protein (such as keyhole limpet hemocyanin), isolating and cloning a single antibody producing cell, and assaying the resulting monoclonal antibodies to ensure that they have the desired specificity. An exemplary protocol for producing a monoclonal antibody that that specifically bind to the N-terminus amino acid sequence (SEQ ID No. 1)

LLARDFEKNY is described infra.

Preferably, the monoclonal antibody or fragment thereof may preferably comprise one or more complementarity-determining regions (CDRs) selected from:

```
CDR-L1:
                        (SEQ ID No. 12)
RSSQSIVHSNGNTYLE,

CDR-L2:
                        (SEQ ID No. 13)
KVSNRFS,

CDR-L3:
                        (SEQ ID No. 14)
FQGSHVPLT,
```

-continued
```
CDR-H1:
                        (SEQ ID No. 15)
RNAMS,

CDR-H2:
                        (SEQ ID No. 16)
SISTSDNTYYPDSVKG, and

CDR-H3:
                        (SEQ ID No. 17)
GFDVGAY,
```

Preferably the antibody or fragment thereof comprises at least 2, 3, 4, 5 or 6 of the above listed CDR sequences.

Preferably the monoclonal antibody or fragment thereof has a light chain variable region comprising the CDR sequences

```
CDR-L1:
                        (SEQ ID No. 12)
RSSQSIVHSNGNTYLE,

CDR-L2:
                        (SEQ ID No. 13)
KVSNRFS, and

CDR-L3:
                        (SEQ ID No. 14)
FQGSHVPLT.
```

Preferably the monoclonal antibody or fragment thereof has a light chain that comprises framework sequences between the CDRs, wherein said framework sequences are substantially identical or substantially similar to the framework sequences between the CDRs in the light chain sequence below in which the CDRs are shown in bold and underlined, and the framework sequences are shown in italics:

(SEQ ID NO. 18)

RSSQSIVHSNGNTYLE*WYLQKPGQSPKLLI*KVSNRFS*GVPDRFSGSGS
GTDFTLKISRVDTEDLGVYYC*FQGSHVPLT.

Preferably the monoclonal antibody or fragment thereof has a heavy chain variable region comprising the CDR sequences

```
CDR-H1:
                        (SEQ ID No. 15)
RNAMS,

CDR-H2:
                        (SEQ ID No. 16)
SISTSDNTYYPDSVKG, and

CDR-H3:
                        (SEQ ID No. 17)
GFDVGAY.
```

Preferably the monoclonal antibody or fragment thereof has a heavy chain that comprises framework sequences between the CDRs, wherein said framework sequences are substantially identical or substantially similar to the framework sequences between the CDRs in the heavy chain sequence below in which the CDRs are shown in bold and underlined, and the framework sequences are shown in italics:

(SEQ ID No. 19)
*RNAMS*WVRQTPEKRLEWVA*SISTSDNTYYPDSVKG*RFTISKDNARNILY
LQMSSLRSEDTAMYYCASGFDVGAY

As used herein, the framework amino acid sequences between the CDRs of an antibody are substantially identical or substantially similar to the framework amino acid sequences between the CDRs of another antibody if they have at least 70%, 80%, 90% or at least 95% similarity or identity. The similar or identical amino acids may be contiguous or non-contiguous.

The framework sequences may contain one or more amino acid substitutions, insertions and/or deletions. Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1 Ala, Ser, Thr, Pro, Gly; Group 2 Asp, Asn, Glu, Gln; Group 3 His, Arg, Lys; Group 4 Met, Leu, Ile, Val, Cys; Group 5 Phe Thy Trp.

A program such as the CLUSTAL program to can be used to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention. Identity or similarity is preferably calculated over the entire length of the framework sequences.

In certain preferred embodiments, the monoclonal antibody or fragment thereof may comprise the light chain variable region sequence:

(SEQ ID No. 20)
*DVLMTQTPLSLPVSLGDQASISC*__RSSQSIVHSNGNTYLE__*WYLQKPGQSP*

*KLLIY*__KVSNRFS__*GVPDRFSGSGSGTDFTLKISRVDTEDLGVYYC*__FQGSH__

__VPLT__*FGAGTKLELK*

(CDRs bold and underlined; Framework sequences in italics) and/or the heavy chain variable region sequence:

(SEQ ID No. 21)
*EVKLVESGGGLVKPGGSLKLSCAASGFTFS*__RNAMS__*WVRQTPEKRLEWVA*

__SISTSDNTYYPDSVKG__*RFTISKDNARNILYLQMSSLRSEDTAMYYCAS*__G__

__FDVGAY__*WGQGTLVTVSA*

(CDRs bold and underlined; Framework sequences in italics).

The predetermined cut-off value is preferably at least 9.0 ng/ml, more preferably at least 15.0 ng/ml, even more preferably at least 20.0 ng/ml, even more preferably at least 25.0 ng/ml, and most preferably at least 30 ng/ml. In this regard, through the combined use of various statistical analyses it has been found that a measured amount of binding between the monoclonal antibody (described above) and the N-terminus biomarker of at least 9 ng/ml or greater may be determinative of the presence of lung cancer. By having a statistical cutoff value of at least 9 ng/ml, more preferably at least 15.0 ng/ml, even more preferably at least 20.0 ng/ml, even more preferably at least 25.0 ng/ml, and most preferably at least 30 ng/ml, it is possible to utilise the method of the invention to diagnose lung cancer with a high level of confidence. Or, in other words, applying the statistical cutoff value to the method of the invention is particularly advantageous as it results in a standalone diagnostic assay; i.e. it removes the need for any direct comparisons with healthy individuals and/or patients with known disease severity in order to arrive at a diagnostic conclusion. This may also be particularly advantageous when utilising the assay to evaluate patients that already have medical signs or symptoms that are generally indicative of lung cancer (e.g. as determined by a physical examination and/or consultation with a medical professional) as it may act as a quick and definitive tool for corroborating the initial prognosis and thus potentially remove the need for more invasive procedures, such as endoscopy or biopsy, and expedite the commencement of a suitable treatment regimen. In the particular case of lung cancer, an expedited conclusive diagnosis may result in the disease being detected at an earlier stage, which may in turn improve overall chances of survival.

Preferably, the monoclonal antibody used in the above method does not specifically recognise or bind an N-extended elongated version of the N-terminus amino acid sequence or an N-truncated shortened version of said N-terminus amino acid sequence.

If the patient is determined to have lung cancer as the amount of binding detected is determinative of the presence of lung cancer, then the method may further comprise the step of treating the patient. This may involve administering to the patient suitable treatment for lung cancer. Treatments for lung cancer include surgery, immunotherapy such as pembrolizumab or atezolizumab, cryotherapy, radiofrequent ablation, photodynamic therapy, radiotherapy, chemotherapy, chemoradiotherapy, EGFR inhibitors such as gefitinib, afatanib, erlotinib, dacomitinib, osmertinib; ALK inhibitors such as alectinib, crizotinib, ceritinib, and brigatinib; and nintedanib with or without docetaxel.

The patient biofluid sample may be, but is not limited to, blood, urine, synovial fluid, serum or plasma.

The immunoassay may be, but is not limited to, a competition assay or a sandwich assay. Similarly, the immunoassay may be, but is not limited to, an enzyme-linked immunosorbent assay or a radioimmunoassay.

In a second aspect, the present invention relates to a method for determining whether a patient is responding positively to a treatment for lung cancer, wherein said method comprises using the method described supra to quantify the amount of peptides comprising the N-terminus amino acid sequence (SEQ ID NO: 1)
LLARDFEKNY in at least two biological samples, said biological samples having been obtained from said patient at a first time point and at at least one subsequent time point during a period of administration of the treatment to said patient, and wherein a reduction in the quantity of peptides comprising the N-terminus amino acid sequence (SEQ ID NO: 1)
LLARDFEKNY 7                                                              8 from said first time point to said at least one subsequent time point during the period of treatment is indicative of said patient responding positively to said treatment.

The above method may also be used to determine the efficacy of a novel therapeutic for treating lung cancer. In that regard, a novel therapeutic will be considered efficacious if the quantity of peptides comprising the N-terminus amino acid sequence

```
                                        (SEQ ID NO: 1)
            LLARDFEKNY
``` is reduced from the first time point to the at least one subsequent time point during the period of treatment using the novel therapeutic.

In another aspect, the present invention relates to a method of immunoassay for detecting and/or monitoring the progression of idiopathic pulmonary fibrosis (IPF) in a patient, the method comprising contacting a patient biofluid sample with a monoclonal antibody specifically reactive with an N-terminus amino acid sequence

```
                                        (SEQ ID NO: 1)
            LLARDFEKNY,
``` wherein the monoclonal antibody does not specifically recognise or bind an N-extended elongated version of said N-terminus amino acid sequence or an N-truncated shortened version of said N-terminus amino acid sequence, determining the amount of binding between said monoclonal antibody and peptides comprising said N-terminus amino acid sequence, and correlating said amount of binding with values associated with normal healthy subjects and/or values associated with known IPF severity and/or values obtained from said patient at a previous time point and/or a predetermined cut-off value.

If the patient is determined to have IPF as the amount of binding detected is determinative of the presence of IPF, then the method may further comprise the step of treating the patient. This may involve administering to the patient suitable treatment for IPF. Treatments for IPF include pirfenidone; nintedanib; corticosteroids such as prednisolone; antioxidants such as N-acetylcysteine; oxygen support; pulmonary rehabilitation; and lung transplant.

The patient biofluid sample may be, but is not limited to, blood, urine, synovial fluid, serum or plasma.

The immunoassay may be, but is not limited to, a competition assay or a sandwich assay. Similarly, the immunoassay may be, but is not limited to, an enzyme-linked immunosorbent assay or a radioimmunoassay.

```
                                        (SEQ ID NO: 1)
            LLARDFEKNY,
``` the elongated peptide

```
            (ELLARDFEKNY; SEQ ID NO: 2),
``` the truncated peptide

```
            (LARDFEKNY; SEQ ID NO: 3)
``` a non-sense peptide

```
            (VPKDLPPDTT; SEQ ID NO: 4)
``` an a non-sense coating peptide

```
            (VPKDLPPDTT-biotin; SEQ ID NO: 5);
``` and (FIG. 1B) Von Willebrand factor (VWF), ADAMTS15 (A15), SPARC-like protein 1 (SLP1) and glucagon (GCG), were tested for in the competitive SPARC-M ELISA assay. Signals are shown as optical density (OD) at 450 nm (subtracted the background at 650 nm) as a function of peptide concentration.

Figure 2:
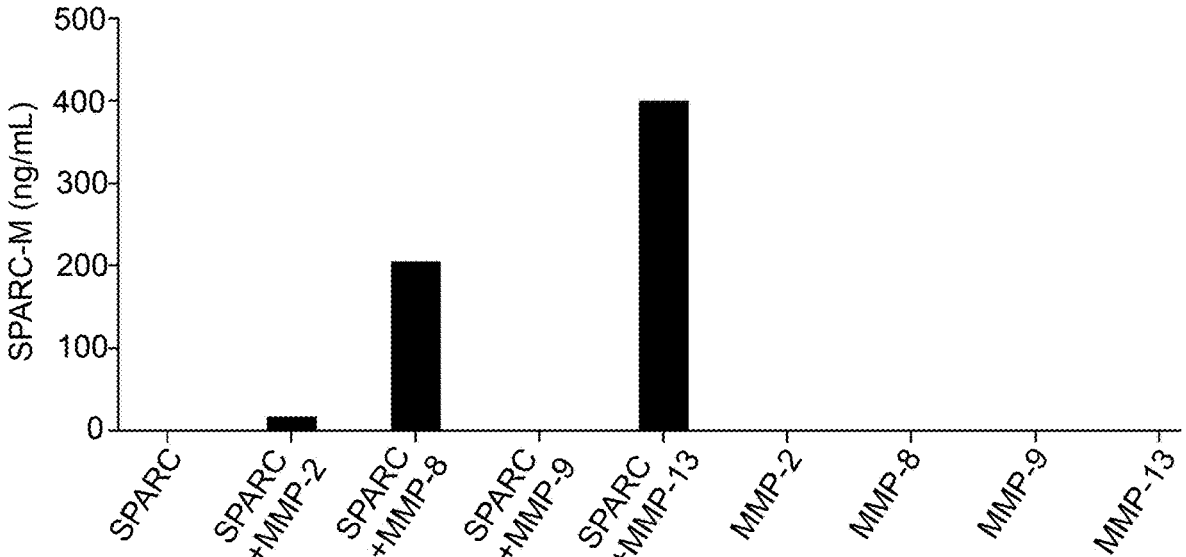

FIG. 2 shows the cleavage of SPARC by collagenases. SPARC was incubated with different MMP's and SPARC-M levels were measured after 24 hours. Data were normalized by subtracting the background measured in buffer alone. The graph below is representative of two experiments.

Figure 3A:
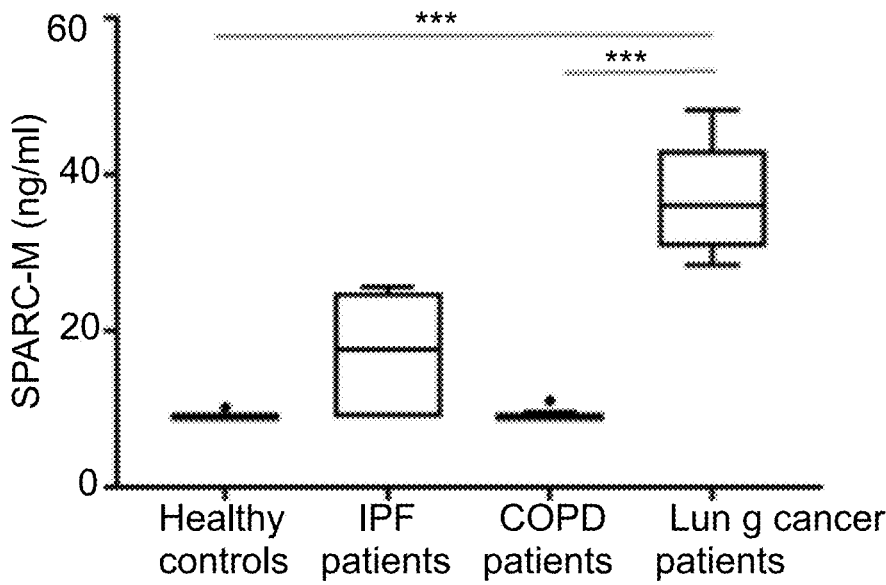
Figure 3B:
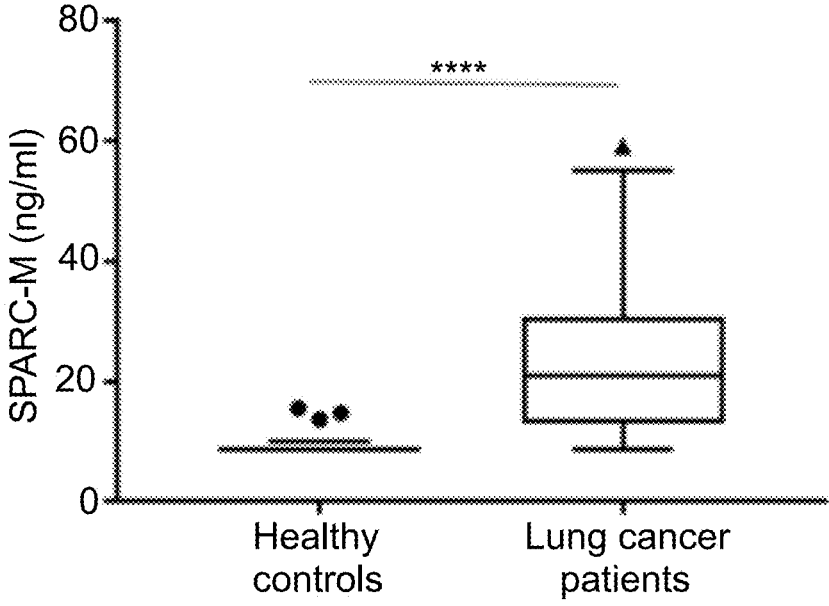
Figure 3C:
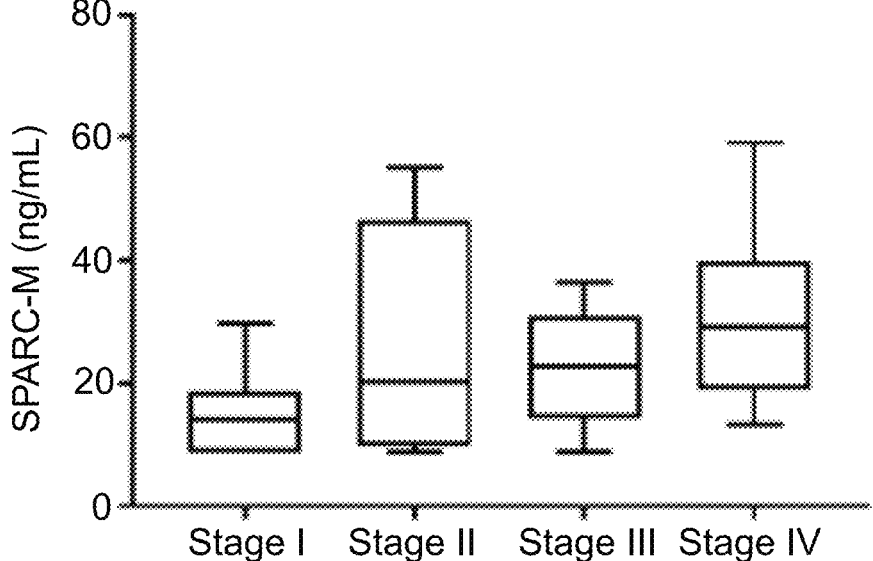

FIGS. 3A-3C show serum SPARC-M levels in patients with fibrotic disorders and healthy controls. In FIG. 3A for Cohort 1 serum SPARC-M was assessed in healthy controls (n=6), IPF patients (n=7), COPD patients (n=8) and lung cancer patients (n=8). Groups were compared using Kruskal-Wallis adjusted for Dunn's multiple comparisons test. In FIG. 3B for Cohort 2 serum SPARC-M was assessed in healthy controls (n=20) and lung cancer patients (n=40). Groups were compared using unpaired, two-tailed Mann-Whitney test. In FIG. 3C lung cancer patients (from cohort 2) were stratified according to their cancer stage (stage I-IV, n=10 in each group). Data were compared using one-way ANOVA adjusted for Tukey's multiple comparisons test. All Data are shown as Tukey box plots. Significance level: *: $p<0.001$, **: $p<0.0001$.

DEFINITIONS

As used herein the term "N-terminus" refers to the extremity of a polypeptide, i.e. at the N-terminal end of the polypeptide, and is not to be construed as meaning in the general direction thereof.

As used herein the term "monoclonal antibody" refers to both whole antibodies and to fragments thereof that retain the binding specificity of the whole antibody, such as for example a Fab fragment, F(ab') 2 fragment, single chain Fv fragment, or other such fragments known to those skilled in the art. As is well known, whole antibodies typically have a "Y-shaped" structure of two identical pairs of polypeptide chains, each pair made up of one "light" and one "heavy" chain. The N-terminal regions of each light chain and heavy chain contain the variable region, while the C-terminal portions of each of the heavy and light chains make up the constant region. The variable region comprises three complementarity determining regions (CDRs), which are primarily responsible for antigen recognition. The constant region allows the antibody to recruit cells and molecules of the immune system. Antibody fragments retaining binding specificity comprise at least the CDRs and sufficient parts of the rest of the variable region to retain said binding specificity.

In the present invention, the monoclonal antibody may comprise any constant region known in the art. Human constant light chains are classified as kappa and lambda light chains. Heavy constant chains are classified as mu, delta, gamma, alpha, or epsilon, and define the antibody's isotype as IgM, IgD, IgG, IgA, and IgE, respectively. The IgG isotype has several subclasses, including, but not limited to IgG1, IgG2, IgG3, and IgG4. The monoclonal antibody may preferably be of the IgG isotype, including any one of IgG1, IgG2, IgG3 or IgG4.

The CDR of an antibody can be determined using methods known in the art such as that described by Kabat et al[19]. Antibodies can be generated from B cell clones as described in the examples. The isotype of the antibody can be determined by ELISA specific for human IgM, IgG or IgA isotype, or human IgG1, IgG2, IgG3 or IgG4 subclasses. The amino acid sequence of the antibodies generated can be determined using standard techniques. For example, RNA can be isolated from the cells, and used to generate cDNA by reverse transcription. The cDNA is then subjected to PCR using primers which amplify the heavy and light chains of the antibody. For example primers specific for the leader sequence for all VH (variable heavy chain) sequences can be used together with primers that bind to a sequence located in the constant region of the isotype which has been previously determined. The light chain can be amplified using primers which bind to the 3' end of the Kappa or Lamda chain together with primers which anneal to the V kappa or V lambda leader sequence. The full length heavy and light chains can be generated and sequenced.

As used herein the term "ELISA" (enzyme-linked immunosorbent assay) refers to an immunoassay in which the target peptide present in a sample (if any) is detected using antibodies linked to an enzyme, such as horseradish peroxidase or alkaline phosphatase. The activity of the enzyme is then assessed by incubation with a substrate generating a measurable product. The presence and/or amount of target peptide in a sample can thereby be detected and/or quantified. ELISA is a technique known to those skilled in the art.

As used herein the term, the term "competitive ELISA" refers to a competitive enzyme-linked immunosorbent assay. In a "competitive ELISA" the target peptide present in a sample (if any) competes with known amount of target of peptide (which for example is bound to a fixed substrate or is labelled) for to binding an antibody, and is a technique known to the person skilled in the art.

As used herein the term "sandwich immunoassay" refers to the use of at least two antibodies for the detection of an antigen in a sample, and is a technique known to the person skilled in the art.

As used herein the term "amount of binding" refers to the quantification of binding between antibody and biomarker, which said quantification is determined by comparing the measured values of biomarker in the biofluid samples against a calibration curve, wherein the calibration curve is produced using standard samples of known concentration of the biomarker. In the specific assay disclosed herein which measures in biofluids the N-terminus biomarker having the N-terminus amino acid sequence LLARDFEKNY (SEQ ID NO: 1), the calibration curve is produced using standard samples of known concentration of the calibration peptide LLARDFEKNY (SEQ ID NO:1). The values measured in the biofluid samples are compared to the calibration curve to determine the actual quantity of biomarker in the sample. The present invention utilises spectrophotometric analysis to both produce the standard curve and measure the amount of binding in the biofluid samples; in the Examples set out below the method utilises HRP and TMB to produce a measurable colour intensity which is proportional to the amount of binding and which can be read by the spectrophotometer. Of course, any other suitable analytical method could also be used.

As used herein the "cut-off value" means an amount of binding that is determined statistically to be indicative of a high likelihood of a lung cancer or IPF in a patient, in that a measured value of biomarker in a patient sample that is at or above the statistical cutoff value corresponds to at least a 70% probability, preferably at least an 80% probability, preferably at least an 85% probability, more preferably at least a 90% probability, and most preferably at least a 95% probability of the presence or likelihood of a lung cancer or IPF.

As used herein the term "values associated with normal healthy subjects and/or values associated with known disease severity" means standardised quantities of SPARC determined by the method described supra for subjects considered to be healthy, i.e. without a lung cancer or IPF and/or standardised quantities of SPARC determined by the method described supra for subjects known to have a lung cancer or IPF of a known severity.

As used herein, "SPARC-M ELISA" refers to the specific competitive ELISA disclosed herein which quantifies in a sample the amount peptides having the N-terminus amino acid sequence (SEQ ID NO: 1)
LLARDFEKNY.

EXAMPLES

The presently disclosed embodiments are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the described embodiments, and are not intended to limit the scope of the present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the following examples, the following materials and methods were employed.

Development of SPARC-M ELISA

Selection of Peptides:

The following cleavage site (1) on SPARC was previously identified by Edman degradation (14): $211$HPVE↓LLARDFEKNYNMYIFP$_{230}$. To generate an antibody specific for the N-terminal of the cleavage fragment, a sequence of 10 amino acids (SEQ ID NO: 1)
↓$_{215}$LLARDFEKNY$_{224}$.

The sequence was blasted for homology to other human secreted extracellular matrix proteins using NPS@: Network Protein Sequence Analysis with the UniprotKB/Swiss-prot database (29). Synthetic peptides used for monoclonal antibody production and validation of the ELISA assay were purchased from Genscript (Piscataway, NJ, USA) and shown in Table 1.

TABLE 1

| Synthetic peptides used for development and validation of the SPARC-M ELISA assay | | |
|---|---|---|
| Peptide name | Amino acid sequence | SEQ ID NO |
| Standard peptide | LLARDFEKNY | 1 |
| Immunogenic peptide | LLARDFEKNY-GGC-KLH | 6 |
| Biotinylated coating peptide | LLARDFEKNY-K-biotin | 7 |
| Elongated peptide | ELLARDFEKNY | 2 |
| Truncated peptide | LARDFEKNY | 3 |
| Non-sense standard peptide | VPKDLPPDTT | 4 |
| Non-sense coating peptide | VPKDLPPDTT-biotin | 5 |
| Von Willebrand factor (VWF) | LLARDCQDHS | 8 |
| Glucagon (GCG) | LAARDFINWL | 9 |
| SPARC-like protein 1 (SLP1) | LLLRDFKKNY | 10 |
| ADAMTS15 (A15) | LLARDQCNLH | 11 |

The target sequence was used as the standard peptide (LLARDFEKNY; SEQ ID NO: 1).

A biotinylated peptide (LLARDFEKNY-K-biotin; SEQ ID NO: 7)

was included as a coating peptide with addition of a lysine residue to the C-terminal end to ensure biotin linking. The specificity of the antibody was tested by including an elongated standard peptide with an additional amino acid added to the N-terminal of the target peptide sequence (ELLARDFEKNY; SEQ ID NO: 2), a truncated standard peptide with a removal of the first N-terminal amino acid (LARDFEKNY; SEQ ID NO: 3)

as well as a non-sense standard peptide (VPKDLPPDTT; SEQ ID NO: 4)

and a non-sense biotinylated coating peptide (VPKDLPPDTT-biotin; SEQ ID NO: 5)

in the assay validation. Four peptides (Von Willebrand factor, glucagon, SPARC-like protein 1 and ADAMTS15) with one amino acid mismatch compared to the first six amino acids in the target sequence were also included to further test the antibody specificity. The immunogenic peptide (LLARDFEKNY-GGC-KLH; SEQ ID NO: 6)

was generated by covalently cross-linking the standard peptide to Keyhole Limpet Hemocyanin (KLH) carrier protein using Succinimidyl 4-(N-maleimidomethyl)cyclo-hexane-1-carboxylate, SMCC (Thermo Scientific, Waltham, MA, USA, cat.no. 22336). Glycine and cysteine residues were added at the C-terminal end to ensure right linking of the carrier protein.

Monoclonal Antibody Production:

Four to six week old Balb/C mice were immunized by subcutaneous injection of 200 µL emulsified antigen containing 50 µg immunogenic peptide (LLARDFEKNY-GGC-KLH; SEQ ID NO: 6)

mixed with Freund's incomplete adjuvant (Sigma-Aldrich, St. Louis, MO, USA). Consecutive immunizations were performed at 2-week intervals until stable sera titer levels were reached. The mouse with the highest titer rested for four weeks and was then boosted with 50 µg immunogenic peptide in 100 µL 0.9% NaCl solution intravenously. Hybridoma cells were produced by fusing spleen cells with SP2/0 myeloma cells as previously described (30). The resultant hybridoma cells were then cultured in 96-well microtiter plates and standard limited dilution was used to secure monoclonal growth. The supernatants were screened for reactivity using the biotinylated peptide (LLARDFEKNY-K-biotin; SEQ ID NO: 7)

as coating agent in the competitive immunoassays.

Clone Characterization:

The reactivity of the monoclonal antibody was evaluated by displacement using human serum samples and the standard peptide (LLARDFEKNY; SEQ ID NO: 1)

in a preliminary ELISA using 10 ng/mL biotinylated coating peptide on streptavidin-coated microtiter plates (Roche, Basel, Switzerland, cat. #11940279) and the supernatant from the antibody producing monoclonal hybridoma cells. The clone with the best reactivity towards the standard peptide was purified using protein-G-columns according to the manufacturer's instructions (GE Healthcare Life Sciences, Little Chalfont, UK, cat. #17-0404-01).

The antibody generated was sequenced and the CDRs determined. Total RNA was isolated from the hybridoma cells following the technical manual of RNeasy Plus Micro Kit (QIAGEN, Cat. No.: 74034). Total RNA was then reverse-transcribed into cDNA using either isotype-specific anti-sense primers or universal primers following the technical manual of SMARTScribe Reverse Transcriptase (Ta-KaRa, Cat. No.: 639536). Antibody fragments of heavy chain and light chain were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. The consensus sequence was provided.

The sequence of the chains are as follows (CDRs in bold; Framework sequence in Italics; Constant region underlined):

```
Heavy chain: Amino acid sequence (458 aa)
(Mouse IgG1 isotype)
                              (SEQ ID. NO: 22)
EVKLVESGGGLVKPGGSLKLSCAASGFTFSRNAMSWVRQTPEKRLEWVA

SISTSDNTYYPDSVKGRFTISKDNARNILYLQMSSLRSEDTAMYYCASG

FDVGAYWGQGTLVTVSAAKTTPPSVYPLAPGSAAQTNSMVTLGCLVKGY

FPEPVTVTWNSGSLSSGVHTFPAVLQSDLYTLSSSVTVPSSTWPSETVT

CNVAHPASSTKVDKKIVPRDCGCKPCICTVPEVSSVFIFPPKPKDVLTI

TLTPKVTCVVVDISKDDPEVQFSWFVDDVEVHTAQTQPREEQFNSTFRS

VSELPIMHQDWLNGKEFKCRVNSAAFPAPIEKTISKTKGRPKAPQVYTI

PPPKEQMAKDKVSLTCMITDFFPEDITVEWQWNGQPAENYKNTQPIMDT

DGSYFVYSKLNVQKSNWEAGNTFTCSVLHEGLHNHHTEKSLSHSPGK.

CDR-H1:
                              (SEQ ID No. 15)
RNAMS

CDR-H2:
                              (SEQ ID No. 16)
SISTSDNTYYPDSVKG

CDR-H3:
                              (SEQ ID No. 17)
GFDVGAY

Light chain: Amino acid sequence (238 aa)
(mouse Kappa isotype)
                              (SEQ ID. NO: 23)
DVLMTQTPLSLPVSLGDQASISCRSSQSIVHSNGNTYLEWYLQKPGQSP

KLLIYKVSNRFSGVPDRFSGSGSGTDFTLKISRVDTEDLGVYYCFQGSH

VPLTFGAGTKLELKRADAAPTVSIFPPSSEQLTSGGASVVCFLNNFYPK

DINVKWKIDGSERQNGVLNSWTDQDSKDSTYSMSSTLTLTKDEYERHNS

YTCEATHKTSTSPIVKSFNRNEC.

CDR-L1:
                              (SEQ ID No. 12)
RSSQSIVHSNGNTYLE

CDR-L2:
                              (SEQ ID No. 13)
KVSNRFS

CDR-L3:
                              (SEQ ID No. 14)
FQGSHVPLT
```

SPARC-M ELISA Protocol:

Optimal incubation-buffer, -time and -temperature, as well as the optimal concentrations of antibody and coating peptide were determined and the finalized SPARC-M competitive ELISA protocol was as follows:

A 96-well streptavidin-coated microtiter plate was coated with 1.1 ng/ml biotinylated coating peptide dissolved in assay buffer (50 mM Tris-BTB, 4 g/L NaCl, pH 8.0) and incubated for 30 min. at 20° C. in darkness shaking (300 rpm). Twenty µL standard peptide or pre-diluted serum (1:4) were added to appropriate wells, followed by the addition of 100 µL monoclonal antibody dissolved in assay buffer to a concentration of 14 ng/ml to each well and incubated 1 hour at 20° C. in darkness shaking (300 rpm). One hundred µL of goat anti-mouse POD-conjugated IgG antibody (Thermo Scientific, Waltham, MA, USA, cat. #31437) diluted 1:6000 in assay buffer was added to each well and incubated 1 hour at 20° C. in darkness shaking. All incubation steps were followed by five washes in washing buffer (20 mM Tris, 50 mM NaCl, pH 7.2). Finally, 100 µL tetramethylbenzidine (TMB) (cat. 438OH, Kem-En-Tec Diagnostics, Denmark) was added to each well and the plate was incubated for 15 minutes at 20° C. in darkness shaking. The enzymatic reaction was stopped by adding 0.18 M $H_2SO_4$ and absorbance was measured at 450 nm with 650 nm as reference. A calibration curve was plotted using a 4-parameter logistic curve fit. Data were analyzed using the SoftMax Pro v.6.3 software.

Technical Evaluation of the SPARC-M ELISA:

To evaluate the technical performance of the SPARC-M ELISA, the following validation tests were carried out: Inter- and intra-assay variation, linearity, lower limit of detection, upper limit of detection, analyte stability (freeze/thaw and storage) and interference.

The inter- and intra-assay variation was determined by ten independent runs on different days using seven quality control samples covering the detection range, with each run consisting of double-determinations of the samples. The seven quality control samples consisted of: two human serum samples and five samples with standard peptide in buffer. Intra-assay variation was calculated as the mean coefficient of variance (CV %) within plates and the inter-assay variation was calculated as the mean CV % between the ten individual runs analyzed on different days. To assess linearity of the assay, two-fold dilutions of human serum samples were performed and dilution linearity was calculated as a percentage of recovery of the un-diluted sample. The lower limit of detection (LLOD) was determined from 21 measurements using assay buffer as sample and was calculated as the mean+three standard deviations. The upper limit of detection (ULOD) was determined from ten independent runs of the highest standard peptide concentration and was calculated as the mean back-calibration calculation+three standard deviations. Analyte stability was first determined by the effect of repeated freeze/thaw of serum samples by measuring the SPARC-M level in three human serum samples in four freeze/thaw cycles. The freeze/thaw recovery was calculated with the first cycle as reference. Second, analyte stability in relation to storage was determined by a 48 hour study performed at 4° C. or 20° C. The SPARC-M level in three human serum samples was measured after 0 h, 4 h, 24 h and 48 h of storage and recovery was calculated with samples stored at −20° C. as reference. Interference was determined by adding a low/high content of hemoglobin (0.155/0.310 mM), lipemia/lipids (4.83/10.98 mM) and biotin (30/90 ng/ml) to a serum sample of known concentration. Recovery percentage was calculated with the serum sample as reference.

Cleavage of SPARC In Vitro

Recombinant human SPARC (PeproTech, New Jersey, USA, cat. #120-36) was reconstituted to a final concentration of 1000 µg/mL in MMP-buffer (50 mM Tris-HCl, 150 mM NaCl, 10 mM CaCl2, 10 uM ZnCl, 0.05% Brij35, pH 7.5). MMP-2, MMP-8, MMP-9 and MMP-13 (Giotto, Firenze, Italy, cat. #G04MP02C, #G04MP08C, #G04MP09C, #G04MP13C) were added 1:10 (1 µg MMP and 10 µg SPARC). A positive control protein with known cleavage by the above proteases was included. The solutions incubated at 37° C. for 24 h. The reaction was stopped by adding 1 µM EDTA to the solutions. MMP-buffer with the different proteases were included as controls. Samples were stored at −80° C. until analysis. The activity of the proteases was confirmed by silverstaining according to the manufacturer's instructions (SilverXpress®, Invitrogen, cat. #LC6100) and coomassie blue (data not shown).

Clinical Validation of SPARC-M

Figure 1A:
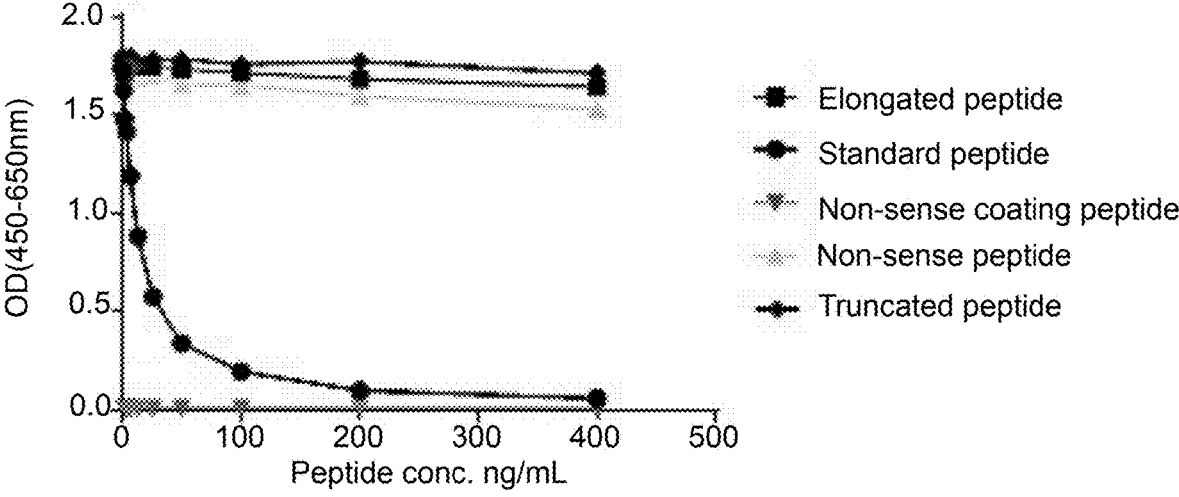
FIGS. 1A-1B demonstrates the specificity of the SPARC-M monoclonal antibody. Monoclonal antibody reactivity towards (FIG. 1A) the standard peptide
Figure 1B:
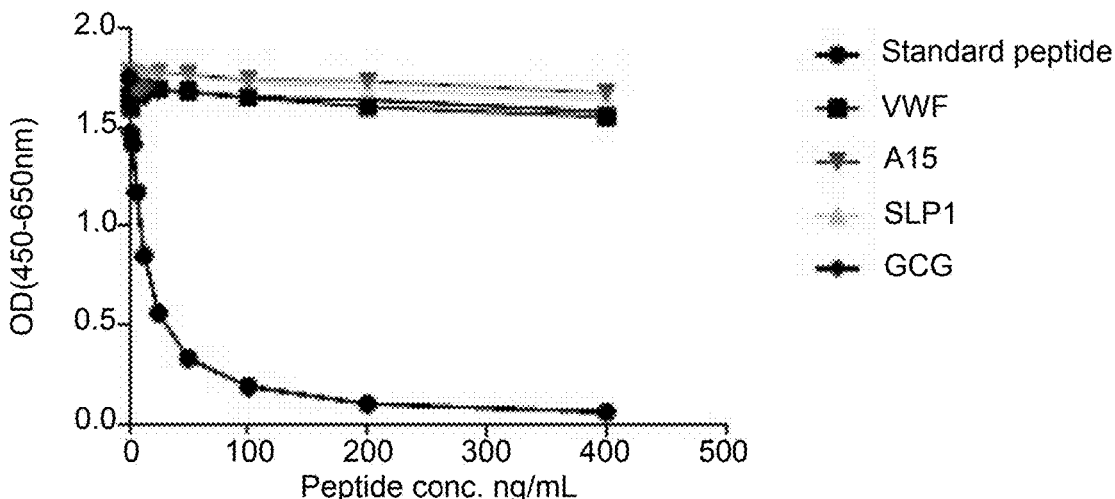

Patient serum samples were obtained from the commercial vendor ProteoGenex (Culver City, CA, USA). Cohort 1 consisted of patients with lung cancer, idiopathic pulmonary fibrosis (IPF), chronic obstructive pulmonary disease (COPD) and colonoscopy-negative controls with no symptomatic or chronic disease (Table 2). Cohort 2 included 40 men and women with different stages of lung cancer, and 20 age-matched colonoscopy-negative controls with no symptomatic or chronic disease (Table 2). Appropriate Institutional Review Board/Independent Ethical Committee approved sample collection and all subjects filed informed consent.

the four peptides (FIG. 1B) suggesting high specificity of the antibody for the target sequence. The specificity of the competitive SPARC-M ELISA was further evaluated by analyzing the reactivity towards the standard peptide, a non-sense peptide, an elongated peptide, a truncated peptide and using a non-sense biotinylated coating peptide. All peptide sequences are shown in Table 1 and results are shown in FIG. 1A. The antibody only reacted with the standard peptide and the standard peptide clearly inhibited the signal in a dose-dependent manner compared to the other peptides. No detectable signal was observed when using the non-sense biotinylated coating peptide. Together, these data suggest that the selected antibody exhibits high neo-epitope specificity.

Technical Evaluation of the SPARC-M ELISA Assay

The technical performance of the SPARC-M ELISA assay was further evaluated according to inter- and intra-assay variation, linearity, lower limit of detection, upper limit of detection, analyte stability (freeze/thaw and storage) and

TABLE 2

Clinical sample overview and patients demographics

| Cohort | Samples | Subject No. | Mean age (range) | Gender, % females | Mean BMI (range) | Tumor stage I | Tumor stage II | Tumor stage III | Tumor stage IV |
|---|---|---|---|---|---|---|---|---|---|
| 1 | Lung cancer patients | 8 | 61 (47-77) | 13 | — | — | — | — | — |
| 1 | IPF patients | 7 | 73 (55-81) | 57 | — | — | — | — | — |
| 1 | COPD patients | 8 | 75 (69-82) | 50 | — | — | — | — | — |
| 1 | Healthy controls | 6 | 55 (44-65) | 83 | — | — | — | — | — |
| 2 | Lung cancer patients | 40 | 62 (55-66) | 50 | 25 (16-35) | 10 | 10 | 10 | 10 |
| 2 | Healthy controls | 20 | 62 (60-65) | 50 | 26 (22-32) | — | — | — | — |

Statistical Analysis

The level of SPARC-M in serum samples was compared using unpaired, two-tailed Mann-Whitney test and Kruskal-Wallis adjusted for Dunn's multiple comparisons test. Patients were stratified according to their tumor stage and the level of SPARC-M in each group was compared using one-way ANOVA adjusted for Tukey's multiple comparisons test. D'Agostino-Pearson omnibus test was used to assess the normality of the data. The diagnostic power was investigated by the area under the receiver operating characteristics (AUROC).

Graph design and statistical analyses were performed using GraphPad Prism version 7 (GraphPad Software, Inc., CA, USA).

Results

Specificity of the SPARC-M ELISA Assay

The target sequence, LLARDFEKNY (SEQ ID NO:1), was blasted for homology to other human secreted extracellular matrix proteins using NPS@: Network Protein Sequence Analysis with the UniprotKB/Swiss-prot database. The target sequence was found to be unique to human SPARC when compared to other secreted ECM proteins. Allowing one amino acid mismatch, four secreted extracellular matrix proteins, Von Willebrand factor, glucagon, SPARC-like protein 1 and ADAMTS15, were identified with mismatches at the $6^{th}$, $2^{nd}$, $3^{rd}$ and $6^{th}$ position, respectively (Table 1). There was no reactivity against the sequence of interference. The different validation steps and SPARC-M performance are shown in Table 3.

TABLE 3

Technical validation data of the SPARC-M ELISA assay

| Technical validation step | SPARC-M performance |
|---|---|
| Detection range (LLOD-ULOD) | 2.7-300.7 ng/ml |
| Intra-assay variation | 6% |
| Inter-assay variation | 10% |
| Dilution of serum samples | 1:4 |
| Dilution recovery (1:4 pre-dilution) | 96% (77-102%) |
| Freeze/thaw recovery (4 cycles) | 92% (86-103%) |
| Analyte stability up to 48 h, 4° C. and 4 h, 20° C. | 88% (84-96%) |
| Interference Lipids, low/high | 96%/97% |
| Interference Biotin, low/high | 96%/98% |
| Interference Hemoglobin, low/high | 96%/80% |

Percentages are reported as mean with range shown in brackets

The measuring range (LLOD to ULOD) of the assay was determined to be 2.7-300.7 ng/ml. The intra- and inter-assay variation was 6% and 10%, respectively. The acceptance criterion was below 10% for the intra-assay variation and below 15% for the inter-assay variation and therefore acceptable. To obtain linearity, human serum needed to be diluted 1:4 and the mean dilution recovery for 1:4 pre-diluted human serum was 96%. The analyte stability was analyzed according to freeze/thaw cycles and storage stability at 4° C. and 20° C. with an acceptance criterion of the recovery within 100%+20%. The analyte recovery in serum was 92% after 4 freeze/thaw cycles. After storage at 4° C. for 48 hours the recovery was 84%. Analyte stability was also tested at 20° C. for 4, 24 and 48 hours. The recovery after 4 hours was 88%. However after 24 hours the analyte could not be recovered within the acceptance range (50% recovery). These data indicate that the analyte in serum is stable at 4° C. up to 48 hours, however upon analysis serum samples should not be stored above 20° C. for more than four hours. No interference was detected from either low or high contents of biotin, lipids or hemoglobin with recoveries ranging from 80-98%. The acceptance criterion was a recovery within 100%+20%.

Degradation of SPARC by Collagenases (MMP-8 and MMP-13)

To further evaluate the specificity of the antibody and to investigate which proteases generate SPARC-M, different gelatinases (MMP-2 and MMP-9) and collagenases (MMP-8 and MMP-13) were incubated with recombinant full-length SPARC. As shown in FIG. 2, the collagenases were able to generate the fragment, with MMP-13 giving the highest level of SPARC-M. In contrast, no SPARC-M was generated without the proteases or when incubated with MMP-9. MMP-2 was able to generate a small amount of SPARC-M as compared to the collagenases.

These results indicate that the antibody is specific for the cleavage site and that collagenases compared to gelatinases have a higher preference for SPARC at this specific site.

Clinical Evaluation of SPARC-M

To investigate whether SPARC-M had clinical disease relevance and biomarker potential, SPARC-M was measured in patients with different fibrotic lung disorders and healthy controls. Cohort 1 consisted of patients with lung cancer, IPF, COPD and healthy controls. As shown in FIG. 3A, SPARC-M was significantly elevated in lung cancer patients compared to healthy controls and COPD patients. IPF patients also had an increased level of SPARC-M compared to healthy controls. To confirm these findings, SPARC-M was measured in a second and larger cohort including 40 lung cancer patients and 20 healthy controls. A significant increase in SPARC-M in lung cancer patients as compared to healthy controls was confirmed (FIG. 3B). The area under the receiver operating characteristics (AUROC) was used to evaluate the discriminative power of SPARC-M in relation to lung cancer patients and healthy controls (cohort 2). SPARC-M was able to discriminate between patients and healthy controls with an AUROC of 0.87 (95% CI: 0.78-0.96).

To examine if the level of SPARC-M was different in patients with metastasis (high tumor burden) compared to patients with localized tumors, patients from cohort 2 were stratified according to their tumor stage (stage I-IV). No significant difference was observed between the tumor stages, however an increasing trend of SPARC-M was observed with increasing tumor stage (FIG. 3C).

CONCLUSION

The present study describes the development and biological validation of a competitive ELISA assay quantifying a fragment of SPARC in serum. The main findings of this study were: 1) the investigated fragment was detectable in serum and significantly elevated in lung cancer patients compared to healthy controls, 2) the assay was technically robust and specific towards a unique MMP-8/MMP-13 degraded fragment of SPARC, SPARC-M, and 3) the assay shows potential for use in evaluating IPF.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference.

REFERENCES

1. Lane T F and Sage E H. The biology of SPARC, a protein that modulates cell-matrix interactions. FASEB J. 1994; 8:163-73.
2. Bradshaw A D. The role of SPARC in extracellular matrix assembly. Journal of Cell Communication and Signaling. 2009; 3:239-46.
3. Brekken R A and Sage E H. SPARC, a matricellular protein: at the crossroads of cell-matrix. Matrix Biology. 2000; 19:569-80.
4. Chiodoni et al. Matricellular proteins: From homeostasis to inflammation, cancer, and metastasis. Cancer and Metastasis Reviews. 2010; 29:295-307.
5. Yan Q, Sage E H. SPARC, a Matricellular Glycoprotein with Important Biological Functions. J Histochem Cytochem. 1999; 47:1495-505. doi: 10.1177/002215549904701201.
6. Emerson R O, Sage E H, Ghosh J G, Clark J I. Chaperone-like activity revealed in the matricellular protein SPARC. J Cell Biochem. 2006; 98:701-5.
7. Rosset E M, Bradshaw A D. SPARC/osteonectin in mineralized tissue. Matrix Biology. 2016; 52-54:78-87.
8. Bradshaw A D, Baicu C F, Rentz T J, Van Laer A O, Boggs J, Lacy J M, et al. Pressure overload-induced alterations in fibrillar collagen content and myocardial diastolic function: Role of secreted protein acidic and rich in cysteine (SPARC) in post-synthetic procollagen processing. Circulation. 2009; 119:269-80.
9. Bradshaw A D, Puolakkainen P, Dasgupta J, Davidson J M, Wight T N, Sage E H. SPARC-null mice display abnormalities in the dermis characterized by decreased collagen fibril diameter and reduced tensile strength. J Invest Dermatol. 2003; 120:949-55.
10. Delany A M, Amling M, Priemel M, Howe C, Baron R, *Canalis* E. Osteopenia and decreased bone formation in osteonectin-deficient mice. J Clin Invest. 2000; 105:915-23.
11. Rentz T J, Poobalarahi F, Bornstein P, Sage E H, Bradshaw A D. SPARC regulates processing of procollagen I and collagen fibrillogenesis in dermal fibroblasts. J Biol Chem. 2007; 282:22062-71.
12. Trombetta-eSilva J. The Function of SPARC as a Mediator of Fibrosis. Open Rheumatol J. 2012; 6:146-55.
13. Trombetta J M, Bradshaw A D, Johnson R H. SPARC/Osteonectin Functions to Maintain Homeostasis of the Collagenous Extracellular Matrix in the Periodontal Ligament. J Histochem Cytochem. 2010; 58:871-9. doi: 10.1369/jhc.2010.956144.
14. Sasaki T, Göhring W, Mann K, Maurer P, Hohenester E, Knäuper V, et al. Limited cleavage of extracellular matrix protein BM-40 by matrix metalloproteinases increases its affinity for collagens. J Biol Chem. 1997; 272:9237-43.
15. Sasaki T, Miosge N, Timpl R. Immunochemical and tissue analysis of protease generated neoepitopes of BM-40 (osteonectin, SPARC) which are correlated to a higher affinity binding to collagens. Matrix Biol. 1999; 18:499-508.

16. Gilles C, Bassuk J a, Pulyaeva H, Sage E H, Foidart J M, Thompson E W. SPARC/osteonectin induces matrix metalloproteinase 2 activation in human breast cancer cell lines. Cancer Res. 1998; 58:5529-36.

17. Jacob K, Webber M, Benayahu D, Kleinman H K. Osteonectin promotes prostate cancer cell migration and invasion: A possible mechanism for metastasis to bone. Cancer Res. 1999; 59:4453-7.

18. Tremble P M, Lane T F, Sage E H, Werb Z. SPARC, a secreted protein associated with morphogenesis and tissue remodeling, induces expression of metalloproteinases in fibroblasts through a novel extracellular matrix-dependent pathway. J Cell Biol. 1993; 121:1433-44.

19. Sangaletti S, Tripodo C, Cappetti B, Casalini P, Chiodoni C, Piconese S, et al. SPARC oppositely regulates inflammation and fibrosis in bleomycin-induced lung damage. Am J Pathol. 2011; 179:3000-10.

20. Strandjord T P, Madtes D K, Weiss D J, Sage E H. Collagen accumulation is decreased in SPARC-null mice with bleomycin-induced pulmonary fibrosis. Am J Physiol. 1999; 277 3 Pt 1: L628-35. http://www.ncbi.nlm-.nih.gov/pubmed/10484471.

21. Wang J-C, Lai S, Guo X, Zhang X, de Crombrugghe B, Sonnylal S, et al. Attenuation of fibrosis in vitro and in vivo with SPARC siRNA. Arthritis Res Ther. 2010; 12:1-9.

22. Pichler R H, Hugo C, Shankland S J, Reed M J, Bassuk J A, Andoh T F, et al. SPARC is expressed in renal interstitial fibrosis and in renal vascular injury. Kidney Int. 1996; 50:1978-89.

23. Camino A M, Atorrasagasti C, Maccio D, Prada F, Salvatierra E, Rizzo M, et al. Adenovirus-mediated inhibition of SPARC attenuates liver fibrosis in rats. J Gene Med. 2008; 10:993-1004.

24. Neuzillet C, Tijeras-Raballand A, Cros J, Faivre S, Hammel P, Raymond E. Stromal expression of SPARC in pancreatic adenocarcinoma. Cancer and Metastasis Reviews. 2013; 32:585-602.

25. Wong S L I, Sukkar M B. The SPARC protein: an overview of its role in lung cancer and pulmonary fibrosis and its potential role in chronic airways disease. Br J Pharmacol. 2017; 174:3-14.

26. Frizell E, Liu S L, Abraham A, Ozaki I, Eghbali M, Helene Sage E, et al. Expression of SPARC in normal and fibrotic livers. Hepatology. 1995; 21:847-54.

27. Kuhn C, Mason R J. Immunolocalization of SPARC, tenascin, and thrombospondin in pulmonary fibrosis. Am J Pathol. 1995; 147:1759-69.

28. Leeming D, He Y, Veidal S, Nguyen Q, Larsen D, Koizumi M, et al. A novel marker for assessment of liver matrix remodeling: An enzyme-linked immunosorbent assay (ELISA) detecting a MMP generated type I collagen neo-epitope (C1M). Biomarkers. 2011; 16:616-28. doi: 10.3109/1354750X.2011.620628.

29. Combet C, Blanchet C, Geourjon C, Deléage G. NPS@: network protein sequence analysis. Trends Biochem Sci. 2000; 25:147-50. www.ncbi.nlm.nih.gov/pubmed/10694887. Accessed 27 May 2016.

30. Gefter M L, Margulies D H, Scharff M D. A simple method for polyethylene glycol-promoted hybridization of mouse myeloma cells. Somatic Cell Genet. 1977; 3:231-6.

What is claimed is:

1. A monoclonal antibody specifically reactive with an N-terminus amino acid sequence

```
                            (SEQ ID NO: 1)
    LLARDFEKNY
``` comprising the complementarity-determining regions (CDRs):

```
    CDR-L1:
                            (SEQ ID NO. 12)
    RSSQSIVHSNGNTYLE,

CDR-L2:
                            (SEQ ID NO. 13)
    KVSNRFS,

CDR-L3:
                            (SEQ ID NO. 14)
    FQGSHVPLT,

CDR-H1:
                            (SEQ ID NO. 15)
    RNAMS,

CDR-H2:
                            (SEQ ID NO. 16)
    SISTSDNTYYPDSVKG,
    and

CDR-H3:
                            (SEQ ID NO. 17)
    GFDVGAY.
```

2. A method of immunoassay for detecting and/or monitoring progression of lung cancer in a patient, the method comprising:

(i) contacting a patient biofluid sample with a monoclonal antibody specifically reactive with an N-terminus amino acid sequence

```
                            (SEQ ID NO: 1)
    LLARDFEKNY,
``` wherein the monoclonal antibody comprises the complementarity-determining regions (CDRs):

```
    CDR-L1:
                            (SEQ ID NO. 12)
    RSSQSIVHSNGNTYLE,

CDR-L2:
                            (SEQ ID NO. 13)
    KVSNRFS,
```

```
    CDR-L3:
                            (SEQ ID NO. 14)
    FQGSHVPLT,

CDR-H1:
                            (SEQ ID NO. 15)
    RNAMS,

CDR-H2:
                            (SEQ ID NO. 16)
    SISTSDNTYYPDSVKG,
    and

CDR-H3:
                            (SEQ ID NO. 17)
    GFDVGAY,
```

(ii) determining the amount of binding between said monoclonal antibody and peptides comprising said N-terminus amino acid sequence, and (iii) correlating said amount of binding with values associated with normal healthy subjects and/or values associated with known lung cancer severity and/or values obtained from said patient at a previous time point and/or a predetermined cut-off value.

3. The method as claimed in claim 2, wherein the predetermined cut-off value is at least 9.0 ng/ml.

4. The method of claim 2, wherein the patient biofluid sample is blood, urine, synovial fluid, serum or plasma.

5. The method of claim 2, wherein the immunoassay is a competition assay or a sandwich assay.

6. The method of claim 2, wherein the immunoassay is an enzyme-linked immunosorbent assay or a radioimmunoassay.

7. A method for determining whether a patient is responding positively to a treatment for lung cancer, wherein said method comprises using the method of claim 2 to quantify the amount of peptides comprising the N-terminus amino acid sequence

```
                            (SEQ ID NO: 1)
    LLARDFEKNY
``` in at least two biological samples, said biological samples having been obtained from said patient at a first time point and at least one subsequent time point during a period of administration of the treatment to said patient, and wherein a reduction in the quantity of peptides comprising the N-terminus amino acid sequence

```
                            (SEQ ID NO: 1)
    LLARDFEKNY
``` from said first time point to said at least one subsequent time point during the period of treatment is indicative of said patient responding positively to said treatment.

8. A method of immunoassay for detecting and/or monitoring progression of idiopathic pulmonary fibrosis (IPF) in a patient, the method comprising:

(i) contacting a patient biofluid sample with a monoclonal antibody specifically reactive with an N-terminus amino acid sequence

```
                                       (SEQ ID NO: 1)
    LLARDFEKNY,
``` wherein the monoclonal antibody comprises the complementarity-determining regions (CDRs):

```
    CDR-L1:
                                       (SEQ ID NO. 12)
    RSSQSIVHSNGNTYLE,

CDR-L2:
                                       (SEQ ID NO. 13)
    KVSNRFS,

CDR-L3:
                                       (SEQ ID NO. 14)
    FQGSHVPLT,
```

```
                  -continued

CDR-H1:
                                       (SEQ ID NO. 15)
    RNAMS,

CDR-H2:
                                       (SEQ ID NO. 16)
    SISTSDNTYYPDSVKG,
    and

CDR-H3:
                                       (SEQ ID NO. 17)
    GFDVGAY,
```

(ii) determining the amount of binding between said monoclonal antibody and peptides comprising said N-terminus amino acid sequence, and (iii) correlating said amount of binding with values associated with normal healthy subjects and/or values associated with known IPF severity and/or values obtained from said patient at a previous time point and/or a predetermined cut-off value.

9. The method of claim 8, wherein the patient biofluid sample is blood, urine, synovial fluid, serum or plasma.

10. The method of claim 8, wherein the immunoassay is a competition assay or a sandwich assay.

11. The method of claim 8, wherein the immunoassay is an enzyme-linked immunosorbent assay or a radioimmunoassay.

\* \* \* \* \*

SEQUENCE LISTING

```
Sequence total quantity: 23
SEQ ID NO: 1            moltype = AA  length = 10
FEATURE                 Location/Qualifiers
source                  1..10
                        mol_type = protein
                        organism = Homo sapiens
SEQUENCE: 1
LLARDFEKNY                                                          10

SEQ ID NO: 2            moltype = AA  length = 11
FEATURE                 Location/Qualifiers
source                  1..11
                        mol_type = protein
                        organism = Homo sapiens
SEQUENCE: 2
ELLARDFEKN Y                                                        11

SEQ ID NO: 3            moltype = AA  length = 9
FEATURE                 Location/Qualifiers
source                  1..9
                        mol_type = protein
                        organism = Homo sapiens
SEQUENCE: 3
LARDFEKNY                                                           9

SEQ ID NO: 4            moltype = AA  length = 10
FEATURE                 Location/Qualifiers
source                  1..10
                        mol_type = protein
                        organism = synthetic construct
SEQUENCE: 4
VPKDLPPDTT                                                          10

SEQ ID NO: 5            moltype = AA  length = 10
FEATURE                 Location/Qualifiers
source                  1..10
```

```
                              mol_type = protein
                              organism = synthetic construct
MOD_RES                       10
                              note = Residue to bound to biotin
SEQUENCE: 5
VPKDLPPDTT                                                              10

SEQ ID NO: 6                  moltype = AA  length = 13
FEATURE                       Location/Qualifiers
source                        1..13
                              mol_type = protein
                              organism = synthetic construct
MOD_RES                       13
                              note = Residue is bound to keyhole limpet hemocyanin
SEQUENCE: 6
LLARDFEKNY GGC                                                          13

SEQ ID NO: 7                  moltype = AA  length = 11
FEATURE                       Location/Qualifiers
source                        1..11
                              mol_type = protein
                              organism = synthetic construct
MOD_RES                       11
                              note = Residue is bound to biotin
SEQUENCE: 7
LLARDFEKNY K                                                           11

SEQ ID NO: 8                  moltype = AA  length = 10
FEATURE                       Location/Qualifiers
source                        1..10
                              mol_type = protein
                              organism = Homo sapiens
SEQUENCE: 8
LLARDCQDHS                                                             10

SEQ ID NO: 9                  moltype = AA  length = 10
FEATURE                       Location/Qualifiers
source                        1..10
                              mol_type = protein
                              organism = Homo sapiens
SEQUENCE: 9
LAARDFINWL                                                             10

SEQ ID NO: 10                 moltype = AA  length = 10
FEATURE                       Location/Qualifiers
source                        1..10
                              mol_type = protein
                              organism = Homo sapiens
SEQUENCE: 10
LLLRDFKKNY                                                             10

SEQ ID NO: 11                 moltype = AA  length = 10
FEATURE                       Location/Qualifiers
source                        1..10
                              mol_type = protein
                              organism = Homo sapiens
SEQUENCE: 11
LLARDQCNLH                                                             10

SEQ ID NO: 12                 moltype = AA  length = 16
FEATURE                       Location/Qualifiers
source                        1..16
                              mol_type = protein
                              organism = Mus musculus
SEQUENCE: 12
RSSQSIVHSN GNTYLE                                                      16

SEQ ID NO: 13                 moltype = AA  length = 7
FEATURE                       Location/Qualifiers
source                        1..7
                              mol_type = protein
                              organism = Mus musculus
SEQUENCE: 13
KVSNRFS                                                                7

SEQ ID NO: 14                 moltype = AA  length = 9
FEATURE                       Location/Qualifiers
source                        1..9
                              mol_type = protein
```

-continued

```
                          organism = Mus musculus
SEQUENCE: 14
FQGSHVPLT                                                        9

SEQ ID NO: 15         moltype = AA   length = 5
FEATURE               Location/Qualifiers
source                1..5
                      mol_type = protein
                      organism = Mus musculus
SEQUENCE: 15
RNAMS                                                            5

SEQ ID NO: 16         moltype = AA   length = 16
FEATURE               Location/Qualifiers
source                1..16
                      mol_type = protein
                      organism = Mus musculus
SEQUENCE: 16
SISTSDNTYY PDSVKG                                                16

SEQ ID NO: 17         moltype = AA   length = 7
FEATURE               Location/Qualifiers
source                1..7
                      mol_type = protein
                      organism = Mus musculus
SEQUENCE: 17
GFDVGAY                                                          7

SEQ ID NO: 18         moltype = AA   length = 79
FEATURE               Location/Qualifiers
source                1..79
                      mol_type = protein
                      organism = Mus musculus
SEQUENCE: 18
RSSQSIVHSN GNTYLEWYLQ KPGQSPKLLI YKVSNRFSGV PDRFSGSGSG TDFTLKISRV   60
DTEDLGVYYC FQGSHVPLT                                              79

SEQ ID NO: 19         moltype = AA   length = 74
FEATURE               Location/Qualifiers
source                1..74
                      mol_type = protein
                      organism = Mus musculus
SEQUENCE: 19
RNAMSWVRQT PEKRLEWVAS ISTSDNTYYP DSVKGRFTIS KDNARNILYL QMSSLRSEDT   60
AMYYCASGFD VGAY                                                   74

SEQ ID NO: 20         moltype = AA   length = 112
FEATURE               Location/Qualifiers
source                1..112
                      mol_type = protein
                      organism = Mus musculus
SEQUENCE: 20
DVLMTQTPLS LPVSLGDQAS ISCRSSQSIV HSNGNTYLEW YLQKPGQSPK LLIYKVSNRF   60
SGVPDRFSGS GSGTDFTLKI SRVDTEDLGV YYCFQGSHVP LTFGAGTKLE LK          112

SEQ ID NO: 21         moltype = AA   length = 104
FEATURE               Location/Qualifiers
source                1..104
                      mol_type = protein
                      organism = Mus musculus
SEQUENCE: 21
EVKLVESGGG LVKPGGSLKL SCAASGFTFS RNAMSWVRQT PEKRLEWVAS ISTSDNTYYP   60
DSVKGRFTIS KDNARNILYL QMSSLRSEDT AMYYCASGFD VGAY                  104

SEQ ID NO: 22         moltype = AA   length = 439
FEATURE               Location/Qualifiers
source                1..439
                      mol_type = protein
                      organism = Mus musculus
SEQUENCE: 22
EVKLVESGGG LVKPGGSLKL SCAASGFTFS RNAMSWVRQT PEKRLEWVAS ISTSDNTYYP   60
DSVKGRFTIS KDNARNILYL QMSSLRSEDT AMYYCASGFD VGAYWGQGTL VTVSAAKTTP   120
PSVYPLAPGS AAQTNSMVTL GCLVKGYFPE PVTVTWNSGS LSSGVHTFPA VLQSDLYTLS   180
SSVTVPSSTW PSETVTCNVA HPASSTKVDK KIVPRDCGCK PCICTVPEVS SVFIFPPKPK   240
DVLTITLTPK VTCVVVDISK DDPEVQFSWF VDDVEVHTAQ TQPREEQFNS TFRSVSELPI   300
MHQDWLNGKE FKCRVNSAAF PAPIEKTISK TKGRPKAPQV YTIPPPKEQM AKDKVSLTCM   360
ITDFFPEDIT VEWQWNGQPA ENYKNTQPIM DTDGSYFVYS KLNVQKSNWE AGNTFTCSVL   420
HEGLHNHHTE KSLSHSPGK                                              439
```

-continued

```
SEQ ID NO: 23          moltype = AA  length = 219
FEATURE                Location/Qualifiers
source                 1..219
                       mol_type = protein
                       organism = Mus musculus
SEQUENCE: 23
DVLMTQTPLS LPVSLGDQAS ISCRSSQSIV HSNGNTYLEW YLQKPGQSPK LLIYKVSNRF  60
SGVPDRFSGS GSGTDFTLKI SRVDTEDLGV YYCFQGSHVP LTFGAGTKLE LKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                         219
```